United States Patent [19]

Rieck et al.

[11] Patent Number: 4,703,029

[45] Date of Patent: Oct. 27, 1987

[54] MOLDINGS MADE OF SILICATE MATERIAL AND PROCESSES FOR THEIR PREPARATION

[75] Inventors: Hans-Peter Rieck, Hofheim am Taunus; Martin Schott, Steinbach/Taunus; Jürgen Russow, Kelkheim, all of Fed. Rep. of Germany

[73] Assignee: Hoechst Aktiengesellschaft, Frankfurt, Fed. Rep. of Germany

[21] Appl. No.: 755,477

[22] Filed: Jul. 16, 1985

[30] Foreign Application Priority Data

Jul. 18, 1984 [DE] Fed. Rep. of Germany ....... 3426389

[51] Int. Cl.$^4$ ............... B01J 21/06; B01J 23/04; B01J 35/02
[52] U.S. Cl. .................. 502/243; 502/232; 502/325; 502/332; 502/335; 502/407
[58] Field of Search ............ 502/232, 243, 407; 423/325, 332, 335

[56] References Cited

U.S. PATENT DOCUMENTS

| | | | |
|---|---|---|---|
| 1,832,153 | 11/1931 | Stönener | 502/407 X |
| 2,921,033 | 1/1960 | Houdry | 502/232 X |
| 3,579,464 | 5/1971 | Rosen et al. | 502/407 X |
| 3,671,463 | 6/1972 | Colgan | 502/232 |

FOREIGN PATENT DOCUMENTS 37-5163  6/1962  Japan .................. 502/232

OTHER PUBLICATIONS

Eugster, *Science*, 157: 1177–1180 (1967).
Rooney et al, *Amer. Mineral.*, 54:1034–1043 (1969).
Maglione et al, *C. R. Acad. Sci. Paris*, 277: 1721–1724 (1973).
McAtee, Jr. et al, *Amer. Mineral*, 53: 2061–2069 (1968).
Willgallis et al, *Glastechn. Ber.*, 37: 194–200 (1964).
Hoffmann et al, *Z. fur Kristallogr.*, 129: 396–404 (1969).
Johan et al, *Bull. Soc. fr. Mineral Cristallogr.*, 95: 371–382 (1972).
Beneke et al, *Amer. Mineral.*, 62: 763–771 (1977).

*Primary Examiner*—W. J. Shine
*Attorney, Agent, or Firm*—Connolly and Hutz

[57] ABSTRACT

Moldings are described which are composed of a silicic acid with a layer structure, or salts thereof with the general formula $(H,M)_2Si_yO_{2y+1}$, or the corresponding hydrates, M representing lithium, sodium, potassium or ammonium and y being 1.7 to 24. They can be prepared for example by extruding pulverulent layer silicic acids, or salts thereof with the general formula $(H,M)_2Si_yO_{2y+1}$, or the corresponding hydrates, M representing lithium, sodium, potassium or ammonium and y being 1.7 to 24, to produce cylindrical blanks, if appropriate after moistening with water or an organic solvent, and then drying the blanks, or by introducing the same starting materials into a mold, as dry or moist powders, converting them to moldings with the application of pressure and, if appropriate, drying the moldings.

19 Claims, No Drawings

MOLDINGS MADE OF SILICATE MATERIAL AND PROCESSES FOR THEIR PREPARATION

The present invention relates to moldings made of silicic acids with a layer structure, or salts thereof, their use and processes for their preparation.

The silicic acids used here, and their salts, differ in their layer structure from amorphous silicic acids or silicic acids with a skeletal structure, or salts thereof, such as silicalite (U.S. Pat. No. 4,061,724).

Such layer silicic acids and alkali metal salts thereof have been found in nature (H. P. Eugster, Science 157, 1177–1180; T. P. Rooney et al., Amer. Mineral., 54, 1034–1043 (1969); G. Maglione and M. Servant, C. R. Acad. Sci., Ser. D., 277, 1721–1724 (1973); J. L. McAtee, Jr. et al., Amer. Mineral., 53 (1968), 2061–2069).

For the minerals kenyaite and magadiite described in these references, the formulae $NaSi_{11}O_{20.5}$—$(OH)_4.3H_2O$ and $NaSi_7O_{13}(OH)_3.3H_2O$ are given inter alia by Eugster. A distinction is drawn here between chemically bonded water (OH groups) and water of crystallization, but this distinction cannot be made with certainty.

The same substances can also be formulated as $Na_2Si_{22}O_{45}.10H_2O$ and $Na_2Si_{14}O_{29}.9H_2O$.

A number of alkali metal salts of silicic acids with a layer structure have also already been obtained synthetically. The free silicic acids can be obtained from these alkali metal silicates by acid ion exchange, the layer structure of the compounds being retained.

A process for the preparation of crystalline alkali metal layer silicates with molar ratios $Na_2O/SiO_2$ of 1:14 to 1:22, which is also practicable on an industrial scale, is the subject of German Patent Application No. 34 00 132.8. In this process, an alkali metal silicate dissolved in water or an amorphous alkali metal silicate with a molar ratio $M_2O/SiO_2$ of 0.24 to 2.0, M representing an alkali metal, is treated with a sufficient quantity of an acid compound to give a molar ratio $M_2O$ (not neutralized)/$SiO_2$ of 0.05 to 0.239, the molar ratio $SiO_2/H_2O$ is adjusted to 1:5 to 1:100 by dilution, if appropriate, and the reaction mixture is kept at a reaction temperature of 70° to 250° C. until the alkali metal layer silicate has crystallized out. This method can be used to obtain, for example, an alkali metal layer silicate with a molar ratio $Na_2O/SiO_2$ of about 1:21 and a kenyaite structure. The corresponding free acid can be prepared therefrom by acid ion exchange. The compounds thus obtained are denoted hereafter as Na-SKS-1 or H-SKS-1 respectively.

In the presence of seed crystals with the magadiite structure, this process also makes it possible to prepare a sodium layer silicate with a molar ratio $Na_2O/SiO_2$ of about 1:14, which has the magadiite structure. The corresponding free silicic acid is obtained therefrom by acid ion exchange. These compounds are denoted hereafter as Na-SKS-2 and H-SKS-2.

Several layer silicates with the approximate composition $Na_2Si_2O_5$ are known. These include the following products denoted as Na-SKS-5, Na-SKS-6, Na-SKS-7 and Na-SKS-11.

Na-SKS-5 can be prepared according to Glastechnische Ber. 37, 194–200 (1964). The product resembles α-$Na_2Si_2O_5$ in its X-ray diffraction pattern. The X-ray spectrum has the number 22-1397 according to the list in Powder Diffraction File, Inorganic Phases, (Int. Centre f. Diffraction Data) Swarthmore 1983.

Na-SKS-6 can be prepared according to Zeitschrift für Kristallogr. 129, 396–404 (1969). It resembles δ-$Na_2Si_2O_5$.

Na-SKS-7 can be prepared according to Glastechn. Ber. 37, 194–200 (1964). It resembles β-$Na_2Si_2O_5$.

Na-SKS-11 can be prepared according to Glastechn. Ber. 37, 194–200 (1964), and according to Zeitschrift für Kristallogr. 129, 396–404 (1969). It resembles γ-$NA_2Si_2O_5$.

A method for the preparation of Na-SKS-5, Na-SKS-6 and Na-SKS-11 which is practicable on an industrial scale is described in German Patent Application No. 34 17 649.7. Layer silicates with a different composition are Na-SKS-9, Na-SKS-10 and Na-SKS-13.

Na-SKS-9 can be prepared according to Bull. Soc. franc. Min. Crist., 95, 371–382 (1972). It has the approximate composition $NaHSi_2O_5.H_2O$. The X-ray spectrum has the number 27-709.

Na-SKS-10 can be prepared according to Bull. Soc. franc. Min. Crist., 95, 371–382 (1972), and according to Amer. Mineral., 62, 763–771 (1977). The X-ray spectrum has the number 25-1309. The product has the approximate composition $NaHSi_2O_5.2H_2O$. It resembles the mineral kanemite, for which the formula given in the literature is $NaHSi_2O_4(OH)_2.2H_2O$, corresponding to $NaHSi_2O_5.3H_2O$.

Na-SKS-13 can be prepared according to Bull. Soc. franc. Min., Crist,. 95, 371–382 (1972). The X-ray spectrum has the number 27-708. The product has the approximate composition $NaHSi_2O_5$.

The object of the present invention is to prepare moldings from silicate material which are porous and easy to produce and have a certain mechanical stability so that they can be used for example as packing in a column for the adsorption of vapors from gases without being crushed.

Moldings made of silicate material are usually prepared with the addition of binders so that the blank formed in the shaping process is sufficiently stable that it can at least be released from the mold and (gently) transported without disintegrating. Lime is added as the binder in the molding of quartz powder.

Moldings made of silicate material have now been found which are composed of a silicic acid with a layer structure, or salts thereof with the general formula $(H,M)_2Si_yO_{2y+1}$, or the corresponding hydrates, M representing lithium, sodium, potassium or ammonium and y being 1.7 to 24. The protons in the free silicic acid can thus be totally or partially replaced by M.

The corresponding hydrates have the general formula $(H,M)_2Si_yO_{2y+1}.xH_2O$, x being a number between 0 and 20. In dried powders or moldings, x is below 7 and generally below 4.5.

Intentionally, no attempt has been made here to distinguish between various forms of bound water. The general formula $(H,M)_2Si_yO_{2y+1}.xH_2O$ is also meant to include all those layer silicates which, although possibly formulated in the literature as having OH groups, can nevertheless be described mathematically by the same general formula. Dispensing with a separate notation for silanol OH groups is in no way intended to mean that these might not be present in the starting compounds or the moldings according to the invention.

The moldings can also be composed of a mixture of different layer silicic acids or salts thereof. The moldings according to the invention can have a variety of geometrical shapes and sizes. For example, they can be in the shape of spheres, cylinders, prisms, cubes, cuboids, tubes or plates.

Because of their good mechanical properties, especially water resistance, the preferred moldings are those whose silicate material (salt of a layer silicic acid, or free layer silicic acid) has the magadiite structure or kenyaite structure. The starting compounds are also readily accessible in this case.

The moldings according to the invention can be prepared by extruding the layer silicic acids or salts thereof, in powder form, to produce cylindrical blanks, if appropriate after moistening with water or an organic solvent, and then drying the blanks. It is also possible for the cylindrical blanks produced to be rounded on a pelleting dish, in which case, after drying at 120° C., dimensionally stable, approximately spherical granules are obtained. These have a hardness which is adequate for many purposes. When tested with the Pfizer hardness tester, they give values of 3 to 115 kg, corresponding to a test pressure of 10 to 37 bar.

The moldings according to the invention can also be prepared by introducing the layer silicic acids or salts thereof into a mold, as dry powders (or powders moistened with water or organic solvents), and converting them to moldings with the application of pressure. The molding formed is then released from the mold. The pressure applied are higher than in the case of the abovementioned extruders. When using moistened powders, the moldings produced must subsequently be dried. It is surprising that dimensionally stable moldings can be prepared by this process without the addition of any binders and that these moldings have an even greater hardness than the abovementioned granules. Thus, a dry powder of layer silicic acids or salts of layer silicic acids can be molded in a tube, under load from a die with a pressure of, for example, 500 bar, to produce cylindrical moldings of diameter 16 mm. For these relatively large moldings, however, the Pfizer hardness tester is not suitable as the testing equipment. Instead, the Shore hardness was measured in these cases; for the dry blanks, even without thermal aftertreatment, this can easily reach values above 40. Moldings with Shore hardnesses of at least 40 are preferred because of their mechanical stability.

It has also been shown that if the moldings are heated for several hours at temperatures of 250° to 1200°, preferably 300° to 650° C., they become resistant to water or aqueous solutions in many cases. This is useful if the moldings are used as catalyst supports when the reaction to be catalyzed takes place in the presence of or with the formation of water. The minimum temperature which is necessary to achieve this effect depends on the material. The free layer silicic acids are most suitable for this purpose. Moldings made of H-SKS-2 are water-resistant after heating for only three hours at 250° C., whereas when H-SKS-1 is heated for the same period, a temperature of 400° C. is required. Moldings made of Na-SKS-1 and Na-SKS-2 only become water-resistant after heating at 600° C. The lithium and potassium silicates behave similarly to the sodium silicates. The layer silicates Na-SKS-6, Na-SKS-10, Na-SKS-9 and Na-SKS-13, which are particularly rich in alkali metal, are less suitable for the preparation of water-resistant moldings.

The X-ray spectra recorded show that, in all cases, despite the modified behavior towards water, the heated moldings are still composed of layer silicic acids or salts thereof. The heating time is not critical. In most cases, heating for only one hour is sufficient. No further advantages are gained by heating for more than 3 hours. At the same time, heating also increases the hardness of the molding.

In view of the hardness of the moldings, their high porosity is surprising. The water-resistant moldings prepared by compression and subsequent heating have porosities of at least 40%, measured according to DIN No. 51 056, even when the process has been carried out without the addition of any pore-forming substances. In many cases, porosities of 50 to 60% can be determined if the moldings are impregnated with water in vacuo according to DIN No. 51 056. This shows that the pores are open and makes moldings of this type particularly suitable for impregnation with aqueous solutions or solutions in organic solvents. For this reason, the moldings according to the invention are suitable catalyst supports. For example, they can be impregnated with metal salt solutions such as solutions of copper nitrate, nickel nitrate or cobalt acetate, the solvent, especially water, can then be evaporated off by heating and, if appropriate, the metal salts can be decomposed to their oxides. To promote impregnation of the moldings, the metal salt solutions can contain non-ionic or anionic wetting agents such as, for example, ethoxylated alkylphenols or alkylarylsulfonates. If copper nitrate is used as the starting material, this method gives hydrogenation catalysts, especially for the gas phase. The higher the porosity, the smaller is the apparent density. At working pressures of 500 bar, densities of about 1.0 are obtained. With pressures of 1000–2000 bar in the shaping process, moldings of higher density (1.2–1.3) and lower porosity are obtained. Densities above 1.3 can be produced if the mold filled with powder is evacuated before and during the compression process.

Surprisingly, the moldings according to the invention are suitable as catalysts for a variety of purposes even when they have not been treated with metal salt solutions. It has been found that the moldings according to the invention, especially moldings made of free layer silicic acids, preferably moldings made of H-SKS-1, are suitable for the dehydration, in the gas phase, of aliphatic hydrocarbons containing hydroxyl groups. Preference is given to the dehydration of monohydric aliphatic alcohols with a chain length of $C_1$–$C_5$, especially $C_1$–$C_2$ and propanol, at temperatures of 180°–600° C., preferably 250°–500° C. In this process, the alcohol vapor generally flows through the catalyst bed at a rate of 0.1–10 parts by volume per part by volume (bulk volume) of catalyst and per hour. If, for example, methanol vapor is passed at 250° to 450° C. through a tube containing granules of H-SKS-1, the main reaction products obtained are $C_2$-alkenes to $C_4$-alkenes in addition to dimethyl ether. The silicate-based catalysts (zeolites) used hitherto for this purpose contained aluminum and also differ from the products used according to the invention in their three-dimensional skeletal structure.

The moldings according to the invention are also suitable cracking catalysts. If, for example, saturated aliphatic hydrocarbons having 3 to 10 carbon atoms are passed at temperatures of 400° to 700° C. over the moldings according to the invention, especially over granules of free layer silicic acids, alkenes containing a small number of carbons are formed, together with methane.

The moldings according to the invention are also suitable drying agents and/or adsorbents for vapors of organic compounds, especially after dehydration procedures.

In particular, granules prepared from the layer silicates NA-SKS-1 and Na-SKS-2 are suitable for the adsorption of water and hence for the drying of gases, as well as for the adsorption of vapors of organic substances, for example n-hexane and cyclohexane. The adsorption generally takes place at temperatures of 5° to 95° C., preferably at room temperature. The adsorption capacity of the granules for different vapors is influenced by the previous heating of the granules. Thus, particularly high values are obtained for the absorption of water (28%) and cyclohexane (32%) when granules prepared from Na-SKS-2 are heated for 4 hours at 300° C. prior to being used. If, on the other hand, this material is heated at 450° C., the adsorption capacity decreases again. Not only the moldings made of layer silicates but also those made of the free layer silicic acids, for example H-SKS-6, have an adsorbent action on vapors. If granules are prepared therefrom and these granules are heated at 300° C., a good adsorption capacity for n-hexane and cyclohexane vapors and for water vapor is achieved.

Pulverulent layer silicates such as, for example, Na-SKS-1, and also the corresponding silicic acids such as, for example, H-SKS-1, can be used to prepare plate-like moldings by compression between two plates. Thus, at a pressure of 600 bar, Na-SKS-1 gives plates which, after heating at 600° C., have a porosity of 55%, a density of 1.05 and a Shore hardness of 55. These plates are suitable as thermal insulating material up to temperatures of 600° C. The good insulating action is not restricted to plates but is a property of all moldings according to the invention, a high porosity (>50%) being particularly favorable.

As already stated, the moldings according to the invention have a high porosity. In the preparation of the moldings, pore-forming additives are only necessary when particularly high porosities are desired, although they can also be used for moldings with low porosities. The pore-forming agents are removed from the moldings by the action of heat. Wood flour has proved a suitable pore-forming additive. When the moldings are heated in an oxidizing atmosphere (air), it burns leaving practically no residue. Other suitable pore-forming agents are ammonium carbonate and ammonium bicarbonate. Both salts can be mixed with the pulverulent layer silicic acids (or salts thereof) in quantities of 0 to 25%, for example 10%, prior to the shaping process. They vaporize on subsequent heating.

The invention is illustrated in greater detail by means of the examples.

EXAMPLE 1

300 g of Na-SKS-1 are moistened with 240 g of $H_2O$ and passed through an extruder. Short rods of diameter 3 mm and length 4 mm are formed. These are then rounded in a pelleting drum to form granules with no edges, and dried for 2 hours at 120° C.

The hardness, measured with the hardness tester of Chas. Pfizer Co., Inc., New York, is 3 kg. The hardness tester is a pair of testing tongs for tablets. Taking account of the die area of 3.1 mm², over which the pressure is exerted on the test-piece, there is a factor of 3.2 for conversion of the measured values to bar, i.e. the 3 kg correspond to a resisted tong pressure of 9.6 bar.

EXAMPLE 2

400 g of Na-SKS-2 are moistened with 320 g of $H_2O$ and granules are prepared therefrom as described in Example 1.

The dried granules withstand a pressure of 10.5 bar in the hardness tester.

EXAMPLE 3

200 g of Na-SKS-6 are moistened with 150 g of $H_2O$ and granules are prepared therefrom as described in Example 1.

The dried granules withstand a pressure of 37 bar in the hardness tester.

EXAMPLE 4

H-SKS-1 is prepared according to Example 28 by reacting Na-SKS-1 with hydrochloric acid. Granules are prepared from the washed product, taken moist from the filter, as described in Example 1.

The dried granules withstand a pressure of 20 bar in the hardness tester.

EXAMPLE 5

H-SK-2 is prepared according to Example 30 by reacting Na-SKA-2 with hydrochloric acid. Granules are prepared from the washed product, taken moist from the filter, as described in Example 1.

The dried granules withstand a pressure of 17.6 bar in the hardness tester.

EXAMPLE 6

The granules of Na-SKS-1 prepared in Example 1 are heated for 3 hours at 400° C. They do not disintegrate on subsequent storage for several days in water.

EXAMPLE 7

The granules of Na-SK-2 prepared in Example 2 are heated for 4 hours at 400° C. The heated granules withstand a pressure of 17.9 bar in the hardness tester, i.e. they have become harder through heating. They do not disintegrate on storage for several days in water.

EXAMPLE 8 (Comparative Example)

200 g of precipitated silicic acid (supplier: Merck, Darmstadt) were moistened with 320 g of $H_2O$. An attempt was made to prepare granules therefrom as described in Example 1, but the granules obtained disintegrated so easily, both in the moist state and in the dry state, that the hardness could not be tested. Also, the mechanical stability is not improved by heating at 400° C.

EXAMPLE 9

5.01 g of pulverulent dry Na-SKS-1 are compressed in a tubular press of internal diameter 16 mm, under a die pressure of 500 bar for 5 minutes. The cylindrical molding of height 23.3 mm (diameter 16.3 mm) prepared in this way has a Shore hardness (D according to DIN No. 53 505) of 52 and a density of 1.03.

EXAMPLE 10

4.99 of Na-SKS-2 are compressed as in Example 9 to give a cylindrical molding of diameter 16.3 mm and height 23.1 mm. The molding has a Shore hardness of 60 and a density of 1.04.

EXAMPLE 11

H-SKS-1 is prepared according to Example 28 by reacting Na-SKS-1 with hydrochloric acid. The washed product is then dried at 100° C. and 4.88 g thereof are compressed as in Example 9 to give a cylindrical molding of diameter 16.3 mm and height 22.5 mm. The molding has a Shore hardness of 45 and a density of 1.04.

EXAMPLE 12

H-SKS-2 is prepared according to Example 30 by reacting Na-SK-2 with hydrochloric acid. The washed product is then dried at 100° C. and 4.94 g thereof are compressed as in Example 9 to give a cylindrical molding of diameter 16.3 mm and height 22.8 mm. The molding has a Shore hardness of 57 and a density of 1.04.

EXAMPLE 13

The molding of Na-SKS-1 prepared in Example 9 is heated for 4 hours at 600° C. It then has a Shore hardness of 55 and a density of 0.98. The molding is water-resistant at this stage. Its open porosity, tested according to DIN No. 51 056-A-2 (impregnation in vacuo), is 0.56 cm$^3$/cm$^3$ or 56%.

EXAMPLE 14

A molding of Na-SKS-2 prepared as in Example 10 is heated for 4 hours at 600° C. It then has a Shore hardness of 75 and a density of 1.07. The molding is water-resistant at this stage. Its open porosity (tested as in Example 13) is 58%.

EXAMPLE 15

A molding of H-SKS-1 prepared as in Example 11 is heated for 4 hours at 400° C. It then has a Shore hardness of 55 and a density of 1.02 and is water-resistant. The open porosity (tested as in Example 13) is 56%. The X-ray spectrum shows that the structure of the H-SKS-1 has been retained.

EXAMPLE 16

A molding of H-SKS-2 prepared as in Example 12 is heated for 4 hours at 250° C. It then has a Shore hardness of 48 and a density of 1.03. Its open porosity (tested as in Example 13) is 60%. Another molding of H-SK-2 is instead heated for 4 hours at 400° C. The Shore hardness is then 60, the density 1.0 and the open porosity 56%.

In both cases, the structure of the H-SKS-2 is retained, as shown by the X-ray spectra. Both moldings are water-resistant.

EXAMPLE 17

Moldings having a diameter of 51.4 mm and a height of approx. 49 mm are prepared from H-SKS-1 by compression in a cylindrical tube with a die. The density of the moldings increases with the pressure of the die:

| | | |
|---|---|---|
| pressure | 480 bar | density 1.05 |
| pressure | 960 bar | density 1.21 |
| pressure | 1440 bar | density 1.29 |

If a vacuum is applied before and during the compression process, the density can be increased still further. After compression at 960 bar, the density is 1.36.

EXAMPLE 18

5.05 g of Na-SK-6 are compressed as in Example 9 to give a cylindrical molding of diameter 16.2 mm and height 21.9 mm. The Shore hardness is 45 and the density is 1.12.

EXAMPLE 19

(comparative example)

5 g of pulverulent precipitated silicic acid (FK 320 DS from Degussa) were compressed as in Example 9. The molding disintegrates when released from the mold.

EXAMPLE 20

Pulverulent Na-SKS-1 is compressed dry in a thin layer between 2 plates. The pressure is 600 bar. A round plate of thickness 3.1 mm and diameter approx. 70 mm is formed. The density is 1.1. After heating at 600° C., the density is 1.05 and the porosity is 55%. The plate is suitable as a thermal insulating material up to at least 600° C.

EXAMPLE 21

A molding made of Na-SKS-1, described in Example 13 and heated at 600° C., is impregnated in vacuo with 0.6 cm$^3$/cm$^3$ of a 10% solution of $Cu(NO_3)_2.3H_2O$. The impregnated molding is dried and then kept at 350° C. for 2 hours. The copper nitrate decomposes to CuO during this process. After reduction in a hydrogen/nitrogen mixture, the molding is suitable as a hydrogenation catalyst for the gas phase.

Hydrogenation catalysts of similar activity can be obtained by impregnating pulverulent layer silicates or layer silicic acids with solutions of metal salts, for example copper nitrate solutions, drying the impregnated materials and then processing them under pressure to form moldings. In the impregnation of both moldings and powders of layer silicates, some of the alkali metal ions can be exchanged with $Cu^{++}$ ions. This effect can be controlled via the pH of the impregnating solution.

EXAMPLE 22

The granules of Na-SKS-1 described in Example 1 are suitable for the adsorption of vapors from the gas phase. The adsorption capacity was tested by keeping the granules in a desiccator over dishes containing hexane, cyclohexane or 20% sulfuric acid ($H_2O$ partial pressure approx. 20 mbar) for 15 hours in each case. The weight increase of the granules was then determined. The results are given in the table which follows. Granules of Na-SKS-1 which have been heated at 400° C. or 600° C. also have a good adsorption capacity. Likewise, granules of Na-SKS-2 which have been heated at 300° C. or 450° C. are suitable. Finally, granules of H-SK-6 show a surprisingly good adsorption capacity for vapors.

The starting material for granules of H-SKS-6 is produced as follows: The free silicic acid (H-SKS-6) is prepared from Na-SKS-6 by reaction with hydrochloric acid. The washed product is then dried at 120°. Its X-ray spectrum has the number 27-606. $H_2Si_2O_5$ is given as the formula (Johan and Maglione, Bull. Soc. franc. Min. Crist. 95, 371-82 (1972)).

The granules are prepared from the moistened H-SKS-6 by the method of Example 1 and then heated at 300° C.

| Material | Heating °C. | Adsorption (% by weight) | | |
|---|---|---|---|---|
| | | Hexane | Cyclohexane | Water |
| Na-SKS-1 | 120 (drying) | 1 | 12.3 | 10.6 |
| Na-SKS-1 | 400 | 11.3 | 11.5 | 16.6 |
| Na-SKS-1 | 600 | 10.3 | 11.1 | 16.5 |
| Na-SKS-2 | 300 | 8.9 | 32.4 | 28.1 |
| Na-SKS-2 | 450 | 17.1 | 13.8 | 16.0 |
| H-SKS-6 | 300 | 16.5 | 33.1 | 21.1 |

EXAMPLE 23

Granules are prepared from H-SKS-1 as indicated in Example 1. A 100 ml charge of these granules is introduced into a vertical tube which can be heated. The temperature of the charge is kept at 400°–450° C. Methanol vapor is passed over the charge from above. After it has left the tube, the reaction mixture is cooled to condense out water which has formed. The remaining gas is examined in a gas chromatograph. It contains essentially ethene, propene and the various buteness, together with dimethyl ether. Small quantities of aromatics are also detectable.

EXAMPLE 24

Granules are prepared from H-SKS-2 as described in Example 1. A 100 ml charge of the granules is introduced into a vertical tube which can be heated. The charge is heated to 518° C. and kept at this temperature during the reaction. n-Hexane vapor is passed over the charge from above. After it has left the tube, the reaction mixture is cooled to condense out the major part of the n-hexane. The remaining gas is examined in a gas chromatograph. It has the following composition:

| | |
|---|---|
| $H_2$ | 0.4% |
| $CH_4$ | 10% |
| $C_2H_6$ | 7% |
| $C_2H_4$ | 18.5% |
| $C_3H_8$ | 1.4% |
| $C_3H_6$ | 16.4% |
| $i\text{-}C_4H_{10}$ | 0.05% |
| $n\text{-}C_4H_{10}$ | 0.3% |
| $\Sigma C_4H_8$ | 8.5% |
| $\Sigma C_5$ | 2.5% |
| $n\text{-}C_6H_{14}$ | 30% |
| $\Sigma C_6$ | 1.8% |
| $\Sigma C_7$ | 0.1% |

EXAMPLE 25

200 g of H-SKS-1 are moistened with 140 ml of ethanol and granules are prepared therefrom as described in Example 1. The granules, dried at 120° C., withstand a pressure of 13 bar in the hardness tester.

EXAMPLE 26

200 g of H-SKS-1 are mixed with 167 g of silica sol (containing 30% of $SiO_2$) and granules are prepared from this mixture as described in Example 1. The granules, dried at 120° C., withstand a pressure of 30 bar in the hardness tester.

EXAMPLE 27 (Preparation of Na-SKS-1)

First of all, a reaction mixture having the following molar composition:

$$0.303\ Na_2O : 0.0052\ Al_2O_3 : SiO_2 : 30\ H_2O$$

is prepared by adding 83.5 parts by weight of sodium silicate (27% of $SiO_2$, 8.43% of $Na_2O$, 0.24% of $Al_2O_3$) to 149 parts of water. Then, part of a crystalline sodium silicate taken moist from the filter in an earlier experiment (71% weight loss by heating to 1200° C.; only the water content was taken into account in calculating the molar composition) is added. 4.93 parts of 96% sulfuric acid are subsequently added slowly, with stirring. The reaction mixture then has the following molar composition:

$$0.174\ Na_2O : 0.0052\ Al_2O_3 : SiO_2 : 0.129\ Na_2So_4 : 30\ H_2O.$$

The reaction mixture is heated to 205° C. in a stainless steel autoclave in the course of 1.5 hours, kept at this temperature for 2.5 hours and then slowly cooled. After cooling, the reaction mixture is filtered and the material on the filter is washed with water and dried on a suction filter. The product taken moist from the filter has a loss on ignition of 55%. The product dried briefly in the air is examined by thermogravimetric analysis. A weight loss of 43% takes place up to a temperature of about 140° C. No further substantial decrease in weight is observed up to approx. 1000° C. Elemental analysis of the product dried to constant weight at 120° C., i.e. Na-SKS-1, gives the following composition: 3.8% of Na, 0.24% of Al, 41.5% of Si and 0.003% of Fe, from which a molar ratio $SiO_2/Na_2O$ of 17.9 can be calculated. The molar ratio $SiO_2/Al_2O_3$ of 332 shows that, despite the presence of dissolved $Al_2O_3$ in the reaction mixture, this is only incorporated in the end product in very small quantities.

EXAMPLE 28

(Preparation of H-SKS-1)

The crystalline Na silicate from Example 27 is extracted twice with 5% hydrochloric acid at 80° C. for 15 minutes. The product is washed, filtered off and dried at 40° C. Examination by differential thermal analysis shows a pronounced endothermic transition at about 120° C. and a far less pronounced endothermic transition at about 1180° C.

EXAMPLE 29

(Preparation of Na-SKS-2)

The product is prepared with the same educt composition as in Example 27. Seed crystals of a magadiite-type silicate from an earlier experiment are added to the reaction mixture. The reaction mixture is stirred for 19 hours at 165° C. and filtered after cooling, and the material on the filter is washed with water and dried on a suction filter. 10 g of the mother liquor from the reaction mixture, diluted with 250 ml of water, have a pH of 10.4. The product taken moist from the filter, which has a loss on ignition (>1000° C.) of 61.3%, is titrated with sulfuric acid and an equivalence value of 215 meq/100 g of ignited product is determined from the point of inflection of the titration curve at pH 5.0. For a product having the composition $Na_2O.ySiO_2$, this is used to determine an ion exchange capacity of 138 mmols of $Na^+$/mol of $SiO_2$, corresponding to a ratio $SiO_2: Na_2O$ of 14.5:1. If the process is carried out without seed crystals, considerably longer reaction times are necessary.

EXAMPLE 30

(Preparation of H-SKS-2)

100 g of moist product from Example 29 are added to 200 ml of 5% hydrochloric acid and the mixture is stirred for 1.25 hours at room temperature. The product is filtered off and added again to an equal quantity of hydrochloric acid, the mixture is stirred for 25 hours and filtered and the material on the filter is thoroughly washed twice with water, the product being stirred with water and washed on filtration. The product is then dried on a suction filter. It has a loss on ignition of 57%. 10 g of the suction-dried product are added to 190 ml of 5% NaCl solution and then titrated with 1 M NaOH. In the graphical representation of the titration values, an equivalence value of 235 mmol of $H^+$/100 g of ignited product is determined from the point of inflection of the curve at pH 8.3. This is used to determine an ion exchange capacity of about 144 meq/mol of $SiO_2$, corresponding to a ratio $SiO_2:Na_2O$ or a ratio $SiO_2/2H^+$ of 13.9:1.

EXAMPLE 31

The granules of Example 2 were heated for 4 hours at 300° C. for dehydration purposes and were then used for a desiccation of solvents. To this end, a 5 g portion of the granules was added in each case to 25 ml of ethyl acetate (o-xylene, n-hexane) saturated with water. After three hours the solvent was analyzed. The water content of the solvent had dropped from 3.35% (0.056%, 0.07%) to 0.63% (0.0067%, 0.0045%).

EXAMPLE 32

A cylinder of 50 mm diameter and of 48 mm height, which had been obtained by molding Na-SKS-2 under a pressure of 400 bar was placed on a heating plate. Thermoelements were fixed directly on the plate and on the top surface of the cylinder. The plate was heated to 162±2° C. A temperature of 45° C. was established on the top surface of the cylinder. This temperature remained constant for 90 minutes. Then the heating plate was switched off and the cylinder was removed without changing the position of the heating elements. The temperature on the plate, dropped by 2° C. within 23 minutes, whereas the temperature of the thermoelements on the top surface rose continuously to 55° C.

What is claimed is:

1. A molding made of silicate material which is comprised of a crystalline silicic acid with a layer structure with the general formula $H_2Si_yO_{2y+1}$, y being 1.7 to 24, in which the protons are completely or partly substituted by lithium, sodium, potassium or ammonium, or the corresponding hydrates.

2. A molding as claimed in claim 1, which has a porosity of at least 40%, measured according to DIN No. 51056-A-2.

3. A molding as claimed in claim 1, which has a Shore hardness of more than 40.

4. A molding as claimed in claim 1, in which the layer structure is of the magadiite- or kenyaite-type.

5. A catalyst or support therefor comprising a molding as claimed in claim 1.

6. An adsorption or drying agent comprising a molding as claimed in claim 1.

7. A molding made of silicate material which is comprised of a crystalline silicic acid with a layer structure with the general formula $H_2Si_yO_{2y+1}$, or the corresponding hydrates, y being 1.7 to 24, having a porosity of at least 40%, measured according to DIN No. 51056-A-2 and the shaped body having a density of at least 1, said molding being free of binder.

8. A molding as claimed in claim 7, in which the layer structure is of the magadiite- or kenyaite-type.

9. A process for the preparation of moldings as claimed in claim 1, which comprises introducing layer silicic acids, or salts thereof, with the general formula (H,M) $Si_yO_{2y+1}$, or the corresponding hydrates, M representing lithium, sodium, potassium, or ammonium and y being 1.7 to 24, into a mold, as dry or moist powders, converting them to moldings with the application of pressure and, if appropriate, drying the moldings.

10. A process for the preparation of moldings as claimed in claim 1, which comprises extruding pulverulent salts of a layer silicic acid with the general formula $H_2Si_yO_{2y+1}$, or the corresponding hydrates, y being 1.7 to 24, in which the protons are completely or partly substituted by lithium, sodium, potassium or ammonium, to produce cylindrical blanks.

11. A process as claimed in claim 10, wherein the cylindrical blanks are produced after moistening with water or an organic solvent, and the thus-produced blanks are then dried.

12. A process for the preparation of moldings as claimed in claim 1, which comprises introducing pulverulant salts of a layer silicic acid with the general formula $H_2Si_yO_{2y+1}$, or the corresponding hydrates, y being 1.7 to 24, in which the protons are completely or partly substituted by lithium, sodium, potassium or ammonium, into a mold as dry or moist powders, converting them to moldings with the application of pressure.

13. The process as claimed in claim 12, wherein the moldings are heated to temperatures in the range of 250° C. to 1200°.

14. A process as claimed in claim 12, wherein the salt of the layer silicic acid is introduced into the mold as a moist powder, and the molding which results is dried.

15. A process for the preparation of moldings, which comprises extruding pulverulent dry layer silicic acids with the general formula $H_2Si_yO_{2y+1}$, or the corresponding hydrates, y being 1.7 to 24, to produce cylindrical blanks.

16. A process for the preparations of moldings, which comprises introducing pulverulant dry crystalline layer silicic acid with a layer structure with the general formula $H_2Si_yO_{2y+1}$, or the corresponding hydrates, y being 1.7 to 24, into a mold and converting them to moldings with the application of pressure.

17. The process as claimed in claim 16, wherein the moldings are heated to temperatures in the range of from 250° to 1200° C.

18. The process as claimed in claims 10, 12, or 16 wherein said preparation of moldings is without the addition of a binder.

19. A process for the preparation of a molding, which comprises introducing a pulverulent powder of crystalline silicic acid with a layer structure with the general formula $H_2Si_yO_{2y+1}$, or the corresponding hydrates, y being 1.7 to 24, moistened with water or an organic solvent without adding a binder, into a mold, converting the powder to molding with the application of pressure and drying the molding.

\* \* \* \* \*